United States Patent
Sieber et al.

(10) Patent No.: US 8,373,853 B2
(45) Date of Patent: Feb. 12, 2013

(54) DEVICE AND METHOD FOR PROVIDING A PREDETERMINABLE CONCENTRATION OF AT LEAST ONE COMPONENT IN A LIQUID MEDIUM

(75) Inventors: Jochen Sieber, Mannheim (DE); Marcus Dyba, Heidelberg (DE); Volker Seyfried, Nussloch (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 554 days.

(21) Appl. No.: 12/617,049

(22) Filed: Nov. 12, 2009

(65) Prior Publication Data
US 2010/0122588 A1     May 20, 2010

(30) Foreign Application Priority Data
Nov. 18, 2008 (DE) .......................... 10 2008 058 068

(51) Int. Cl.
    *G01N 1/38*          (2006.01)
    *G01N 21/64*        (2006.01)

(52) U.S. Cl. .... 356/243.1; 73/1.03; 73/1.05; 73/863.01; 73/863.02; 250/428; 250/576; 356/36

(58) Field of Classification Search .......... 73/1.02–1.03, 73/1.05, 61.48, 61.59, 64.56, 863.01–863.03; 250/252.1, 364, 368–369, 428, 430, 576; 356/36, 72, 230, 243.1–243.2, 306, 904, 356/929, 951, FOR. 106; 422/75, 82.05, 422/82.08; 435/285.2, 286.1, 288.7, 917; 436/55, 163–164, 172, 174, 180

See application file for complete search history.

(56) References Cited

U.S. PATENT DOCUMENTS

| | | | | |
|---|---|---|---|---|
| 6,444,461 | B1 * | 9/2002 | Knapp et al. | 436/172 X |
| 7,288,405 | B2 * | 10/2007 | Shuler et al. | 435/288.5 |
| 7,377,027 | B2 * | 5/2008 | Mayer | 29/709 |
| 2003/0059849 | A1 * | 3/2003 | Sugahara et al. | 435/7.1 |
| 2004/0029213 | A1 | 2/2004 | Callahan et al. | |
| 2004/0209316 | A1 * | 10/2004 | Ritchlin et al. | 435/7.2 |
| 2005/0170491 | A1 * | 8/2005 | Takagi et al. | 435/287.1 |
| 2006/0275834 | A1 * | 12/2006 | Ritchlin et al. | 435/7.2 |
| 2007/0134804 | A1 * | 6/2007 | Fisher et al. | 436/164 |
| 2008/0072664 | A1 | 3/2008 | Hansen et al. | |

FOREIGN PATENT DOCUMENTS

| | | |
|---|---|---|
| DE | 202009005898 U1 * | 8/2009 |
| WO | 2004025268 | 3/2004 |
| WO | 2008092041 | 7/2008 |

OTHER PUBLICATIONS

European Search Report, Application No. 09014349.6, dated Oct. 20, 2010, in German 6 pages.

\* cited by examiner

*Primary Examiner* — Thomas P Noland
(74) *Attorney, Agent, or Firm* — Schlee IP International, P.C.; Alexander R. Schlee

(57) ABSTRACT

A method and a device for providing a predeterminable concentration of at least one component in a microscopic sample liquid medium are described. The device includes a feeding device for the at least one component. Measurement data are determined, measuring a predeterminable parameter using a microscopic method. The concentration of the at least one component is adjusted or controlled via the feeding device based on the basis of measurement data.

12 Claims, 3 Drawing Sheets

DEVICE AND METHOD FOR PROVIDING A PREDETERMINABLE CONCENTRATION OF AT LEAST ONE COMPONENT IN A LIQUID MEDIUM

CROSS-REFERENCE TO RELATED APPLICATION

This application claims the priority of the German patent application DE 102008058068.6 having a filing date of Nov. 18, 2008. The entire content of this prior German patent application DE 102008058068.6 is herewith incorporated by reference.

BACKGROUND OF THE INVENTION

The present invention relates to a device for providing a predeterminable concentration of at least one component in a liquid medium, in particular in a microscopic sample, said device including a feeding device for the at least one component. The present invention further relates to a corresponding method for providing a predeterminable concentration of at least one component in a liquid medium.

Devices and methods of the above-mentioned type are known in the art. Such known devices may be used, for example, in microscopy applications, where specific amounts of solutions are pipetted; i.e., fed to samples by pipetting robots. Also known in the field of microscopy are devices that are used to inject a specific amount of an active substance into, for example, cells or into the solution containing the cells. Perfusion chambers are also used in microscopy applications. Here too, a predeterminable concentration of at least one component is provided in a liquid medium with the aid of a feeding device for the at least one component.

The known devices and methods are problematic in that the concentration of the at least one component may vary over time due to cell reactions or because of external influences. This results in corruption of measurements, so that, for example, certain long-term measurements cannot be carried out using the known devices and methods. In addition, the sample, and thus, the course of the experiment can thus be actively influenced by adjusting the concentration of the at least one component.

SUMMARY OF THE INVENTION

It is, therefore, an object of the present invention to provide a device for providing a predeterminable concentration of at least one component in a liquid medium, and a corresponding method, whereby even long-term measurements may be carried out in the liquid medium in a simple manner.

In accordance with the present invention, the above object is achieved by a device for providing a predeterminable concentration of at least one component in a liquid medium, said device comprises feeding device for the at least one component, wherein said feeding device is adapted to adjust or control the concentration of the at least one component based on measurement data acquired by measuring a predeterminable parameter using a microscopic method. The respective method for providing a predeterminable concentration of at least one component in a microscopic sample liquid medium by a device including a feeding device for the at least one component comprises measuring measurement data measuring a predeterminable parameter using a microscopic method; and adjusting or controlling the concentration of the at least one component via the feeding device based on the basis of measurement data.

In accordance with the present invention, it was found that long-term measurements are possible if the concentration of the at least one component, whose concentration has changed over time, can be controlled in a substantially predeterminable manner. To this end, in accordance with the present invention, the concentration of the at least one component may be adjusted or controlled by means of the feeding device, the adjustment or control being implemented on the basis of measurement data acquired by measuring a predeterminable parameter that varies with the concentration of the at least one component, the measurement being made using a microscopic method. In other words: measurement data is acquired by measuring a predeterminable parameter using a microscopic method, and the data so obtained is used to adjust or control the concentration of the at least one component with the aid of the feeding device. This provides a particularly elegant and simple way of adjusting or controlling the concentration of the at least one component, because in order to acquire the measurement data needed for the adjustment or control, a microscopic method can be performed using a microscope which is already present for the purpose of microscopically examining the liquid medium or a microscopic sample. Thus, in addition, the sample, and thus, the course of the experiment can be actively influenced by adjusting the concentration of the at least one component.

DETAILED DESCRIPTION OF THE INVENTION

Accordingly, the present invention provides a device whereby even long-term measurements may be carried out in the liquid medium in a simple manner.

In accordance with the present invention, it is also possible to advantageously use measurement data of a plurality of measurement parameters.

Specifically, the device may include a microscope for acquiring the measurement data. This microscope may be a microscope that is already present for the purpose of examining the medium or the sample. Alternatively, a second microscope may be used for acquiring the measurement data.

In another specific embodiment of the device according the present invention, the measurement data may be image data, preferably single-channel or multi-channel images. Such image data may be analyzed for predeterminable aspects to allow for adjustment or control of the concentration of the at least one component. For this purpose, the image data may be further processed by image analysis based on a predeterminable measurement parameter. The measurement data may generally be acquired by image analysis.

Thus, during long-term measurements, for example, the amount of the active components may be maintained constant at a defined level over time, or alternatively, be selectively changed, influenced or controlled even if specific external influences change the conditions for the sample.

The device of the present invention allows the use of different measurement parameters. Examples of such measurement parameters include the brightness in the medium or the brightness of a predeterminable structure or of a predeterminable region in the medium. Depending on the requirements, the control of the concentration of a component that influences brightness may be started when the brightness exceeds or falls below a predetermined level. A relationship between brightness and the concentration of the at least one component is essential here.

Alternatively, the measurement parameter may be the shape of a predeterminable structure or of a predeterminable region in the medium. In this connection, image analysis methods can be used to analyze the acquired measurement data. The control of the concentration of a component that influences the shape of the structure may be started as soon as a predeterminable structure deviates from a reference shape. This is possible in situations where the shape of the predeterminable structure or of the predeterminable region is dependent on the concentration of the at least one component.

Furthermore, the measurement parameter may advantageously indicate when a change, or a plurality of successive changes, in the concentration of the at least one component should be started or stopped. This may occur without the concentration having a direct influence on the measured quantity.

Another measurement parameter that may be used may be the resolution with respect to a predeterminable structure or with respect to a predeterminable region in the medium. For this purpose, it is essential that the resolution achieved by the optical examination be dependent on the concentration of the component. An example would be a change in the refractive index caused by a change in the concentration of the at least one component.

Alternatively or in addition to the techniques mentioned above, a measured quantity that may be used may be the density of signals, the concentration having a direct influence on the measured quantity. The signals may preferably be fluorescence signals.

Also advantageously, the signals may come from single molecules. Preferably, the density of the signals may be optimized for the particular application. For example, the density may be adjusted such that the individual signals can be resolved using diffraction-limited microscopy.

Yet another measurement parameter that may be used may be a specific event—a "rate event"—with respect to a predeterminable structure or a predeterminable region in the medium. Here too, it is essential that the occurrence of the event be dependent on the concentration of the at least one component, so that the occurrence of the event allows conclusions to be drawn on the concentration of the at least one component.

Furthermore, the measurement parameter may advantageously indicate when a change, or a plurality of successive changes, in the concentration of the at least one component should be started or stopped, without the concentration having a direct influence on the measured quantity.

The adjustment or control of the concentration of the at least one component or active component in the sample may be carried out under feedback control on the basis of the acquired data until the desired result, respectively the desired concentration, is reached. In the last-mentioned cases, desired results that may be considered include brightness, shape, resolution, or the occurrence of a specific event in the medium or in a predeterminable structure or predeterminable region in the medium, the density of signals, and the like.

In a particularly simple embodiment of the device, the feeding device may be activatable manually. Delivery of the at least one component into the liquid medium to increase its concentration therein may be accomplished by manually opening a stopcock or valve. Then, the component is added until the desired result is detectable using the microscopic method.

In a more convenient embodiment of the device, the feeding device may be associated with a control device operating on the basis of the measurement data. Such a control device may automatically adjust or control the desired concentration. When a change occurs in the medium or in the sample, the amount of one or more components or active components may then be corrected by the device until the desired concentration is reached. Here too, the control may be carried out using automatic image analysis, the analysis criteria, respectively control parameters, being predeterminable by the user. Thus, control is carried out with the aid of the acquired measurement data, taking into account the predetermined parameter.

The control device may be designed to allow for automatic operation; i.e., automatic adjustment or control of the concentration of the at least one component, as well as for manual operation. Thus, in the last-mentioned case, adjustment or control of the concentration of the at least one component may be performed manually. Here too, feedback may, of course, be provided by the measurement data acquired using the microscopic method. For this purpose, the control device may have an operator control unit for switching between automatic and manual operation.

In a particularly simple embodiment, the feeding device may include a titration or pipetting device. This provides a particularly simple way of feeding a desired component into the liquid medium.

Depending on the particular application, the feeding device may alternatively include a perfusor and/or a perfusion chamber. Such a perfusor enables particularly precise delivery of the required amount of the component.

Furthermore, in an alternative embodiment of the device, the feeding device may include a mixing chamber preferably having a mixing device for at least two components. Using such a mixing chamber, at least two components may be mixed together in the required or desired proportions and manner prior to being fed into the liquid medium. Thus, in this case, only one feed line to the liquid medium is needed, although a plurality of components may be added in the desired proportions.

The feeding device may include a suction device, also for purposes of adjusting or controlling the concentration of the at least one component. Thereby, adjusting the concentration of the at least one component may be accomplished not only by adding an additional amount of the same component, but also by reducing the overall volume of the liquid medium, and therefore also of the component contained therein.

In another advantageous embodiment of the device of the present invention, the feeding device or the control device may be associated with a device for measuring the pH value and/or the osmolarity. This allows the control or adjustment of the concentration of the at least one component to be further optimized using measurement data of one or more additional parameters. In this case, one would not have to rely only on the measurement data acquired using the microscopic method. Any combination of different measurement parameters that takes into account the various demands placed on the adjustment or control of the concentration of the at least one component is suitable. In all cases, consideration must be given to the particular application.

Ultimately, the device of the present invention may be used to advantage in any field of microscopy. The device of the present invention is particularly useful in conjunction with biosensors or fluorogen activating proteins (FAPs), because the device may be used, for example, to control the concentration of the fluorogen. Such FAPs/biosensors are described, for example, in WO 2004/025268 A2 and WO 2008/092041 A2.

The concentration can be adapted exactly to the requirements of the microscopic method used by adding or removing an active component; i.e., by changing the concentration of one or more active components which, by binding to a specific structure, change one or more of their properties. For example, said active component or components may undergo a transition from a fluorescent state to a non-fluorescent state or vice versa, or may change its/their spectral properties, etc.

Furthermore, using the device for precise control in conjunction with FAPs/biosensors in single particle tracking and FCS may have a positive effect on the quality of results in these applications.

The object mentioned above is also achieved by a method for providing a predeterminable concentration of at least one component in a liquid medium, according to which a method of the type mentioned at the outset is further developed and refined in such a way that the concentration of the at least one component is adjusted or controlled via the feeding device on the basis of measurement data acquired by measuring a predeterminable parameter using a microscopic method.

The method of the present invention enables even long-term measurements to be carried out in the liquid medium in a simple manner, because the concentration of at least one component may be adjusted or controlled in a simple way.

Both the method and the device of the present invention are particularly advantageous especially in long-term measurements because bleaching of a dye may be substantially compensated for by adding new dye. Using the device and method of the present invention, the addition of the dye component may be controlled in a simple way, taking into account the acquired measurement data.

With regard to further advantageous embodiments of the method according to the present invention, and to avoid repetitions, reference is made to the above description, wherein advantages of the method have been described in connection with the device of the present invention and the embodiment thereof.

In summary, it can be said that the device and method of the present invention enable the concentration of one or more components in a microscopic sample to be precisely adjusted or controlled on the basis of measurement or image data acquired using the particular microscopic method. Until now, the concentration of components had to be determined by experimentation in a time-consuming manner, whereas the device and method of the present invention enable the concentrations to be controlled or adjusted immediately during the experiment, according to the acquired measurement data.

The teaching of the present invention may be advantageously embodied and refined in various ways. In this regard, reference is made, on the one hand, to the subordinate claims and, on the other hand, to the following description of three exemplary embodiments of a device according to the present invention which makes reference to the drawing. In conjunction with the explanation of the preferred exemplary embodiments of the device of the present invention with reference to the drawing, an explanation is also given of generally preferred embodiments and refinements of the teaching.

DETAILED DESCRIPTION OF THE DRAWINGS

Figure 1:
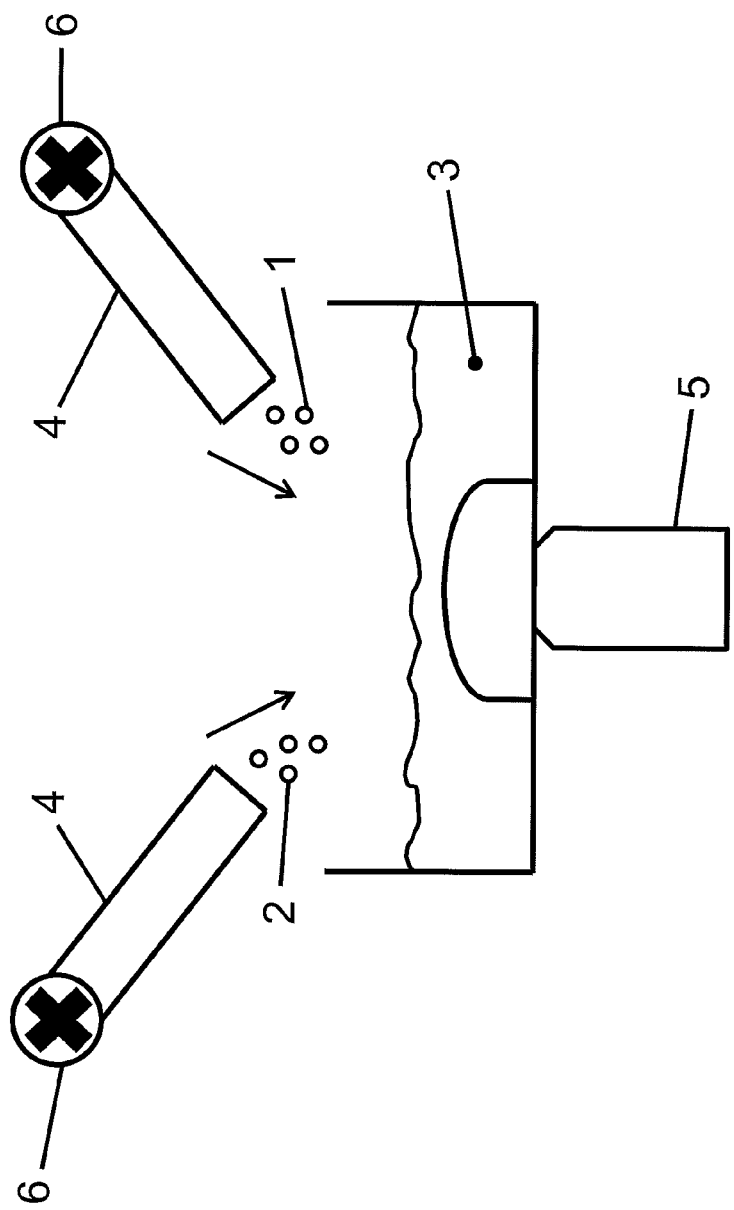
FIG. 1 is a schematic side view showing a first exemplary embodiment of a device according to the present invention.

FIG. 1 shows, in a schematic side view, a first exemplary embodiment of a device according to the present invention for providing a predeterminable concentration of two components 1 and 2 in a liquid medium 3. Here, a microscopic sample is considered into which component 1 as well as component 2 can be fed via a feeding device 4. In order to allow even long-term measurements to be reliably carried out in liquid medium 3, the concentration of components 1 and 2 may be adjusted or controlled via feeding device 4 on the basis of measurement data acquired by measuring a predeterminable parameter using a microscopic method.

Specifically, the device includes a microscope 5 for acquiring the measurement data. In FIG. 1, as well as in FIGS. 2 and 3, microscope 5 is shown only schematically by its objective lens, which is provided for observing liquid medium 3 and/or structures contained therein.

The measurement data is image data, the measurement parameter being, for example, the resolution with respect to a predeterminable structure or with respect to a predeterminable region in medium 3. The resolution is dependent on the concentration of component 1 and/or component 2. When the resolution deviates from a predeterminable quality, the concentration of component 1, or of components 1 and 2, or of component 2 is increased as required. The concentration is increased until the resolution has reached the desired quality again, so that feedback is facilitated here.

The measured quantity used may also be the density of signals, the concentration having a direct influence on the measured quantity. Such signals may, for example, be fluorescence signals.

Feeding device 4 is associated with a control device 6, which may be activated manually or operated automatically. To be more precise, control device 6 may be controlled on the basis of the measurement data acquired by measuring the predetermined parameter in such a way that a control loop is provided.

Figure 2:
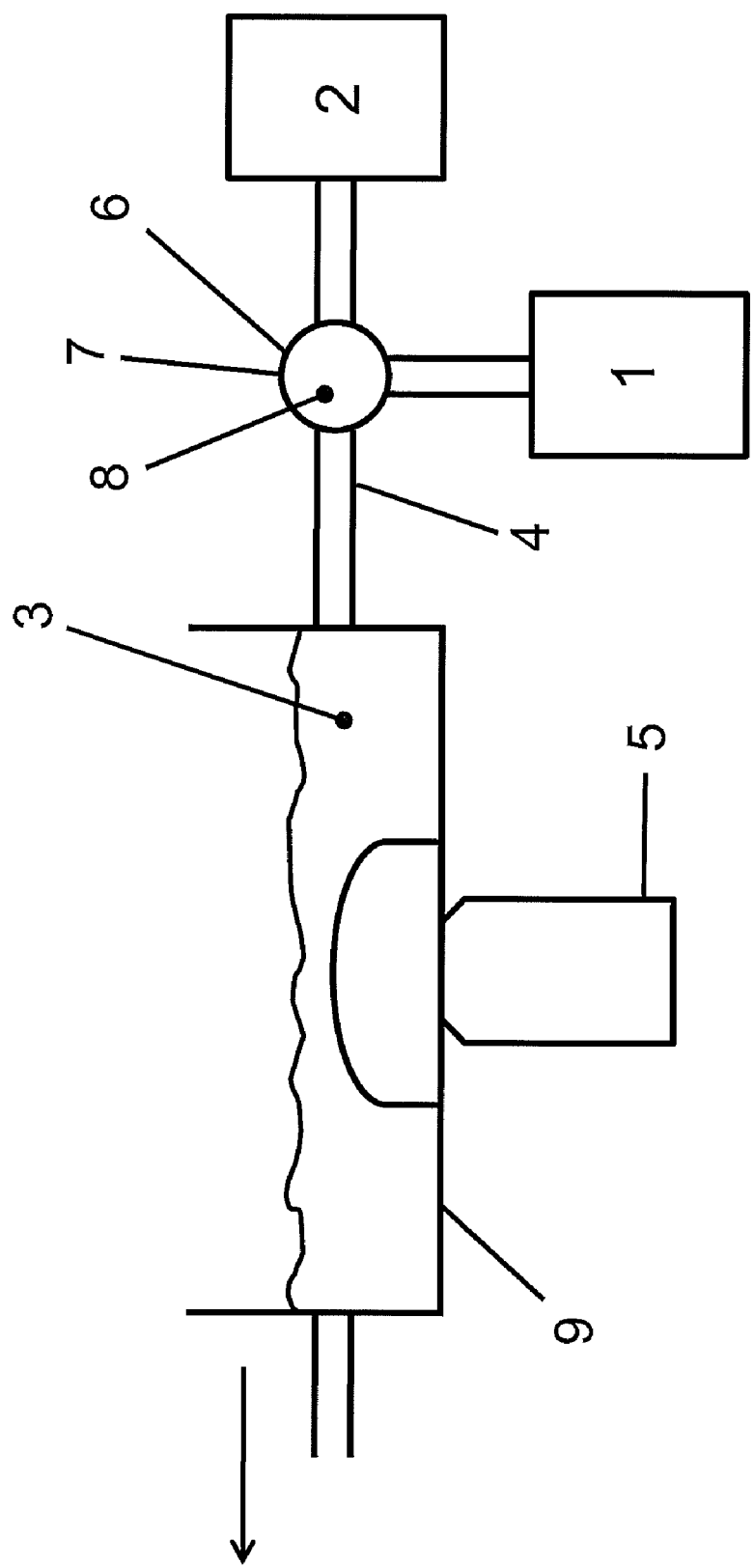
FIG. 2 is a schematic side view illustrating a second exemplary embodiment of a device according to the present invention.

FIG. 2 shows, in a schematic side view, a second exemplary embodiment of a device according to the present invention. In this exemplary embodiment, two components 1 and 2 from separate reservoirs are mixed in a mixing chamber 7 as required using a mixing device 8. Here, the mixing device 8 disposed in mixing chamber 7 also performs the function of control device 6. Once the two components 1 and 2 have been mixed as required, they are fed into liquid medium 3 via feeding device 4.

In the second exemplary embodiment shown here, liquid medium 3 is located in a perfusion chamber 9. Perfusion chamber 9 is designed as a flow-through chamber, it being possible for the liquid level in perfusion chamber 9 to be maintained constant. When components 1 and/or 2 are introduced from feeding device 4 into perfusion chamber 9, the same amount of medium 3 may be removed from perfusion chamber 9.

Figure 3:
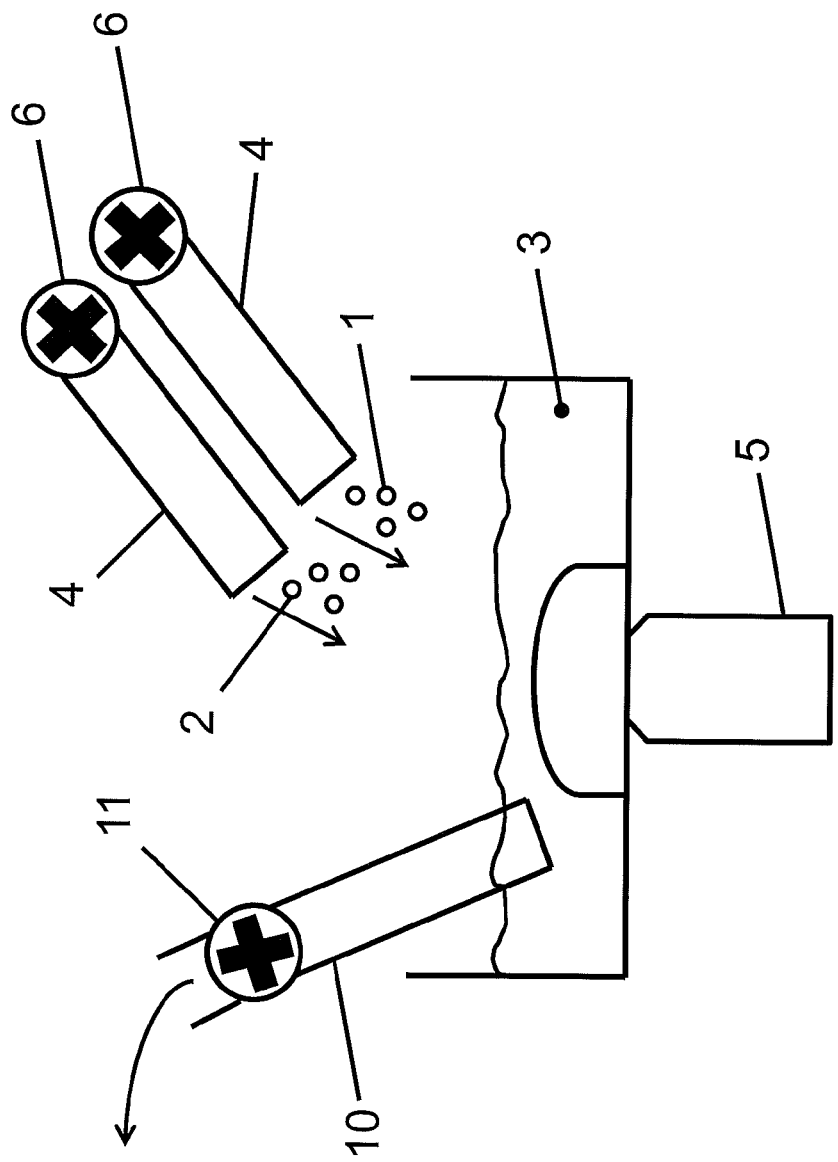
FIG. 3 is a schematic side view of a third exemplary embodiment of a device according to the present invention.

FIG. 3 shows, a schematic side view, a third exemplary embodiment of a device according to the present invention. Two components 1 and 2 may be introduced into liquid medium 3 via feeding devices 4. To this end, the feeding devices 4 for components 1 and 2 are each provided with a control device 6.

This exemplary embodiment features a suction device 10, which allows the liquid level in medium 3 to be maintained constant. Suction device 10 also includes a control device 11.

With regard to further advantageous embodiments and refinements of the teaching of the present invention, and to avoid repetitions, reference is made to the general portion of the description and to the appended claims.

Finally, it should be particularly noted that the above-described exemplary embodiments of the device according to the present invention are merely intended to illustrate the claimed teaching, but not to limit it to such embodiments.

LIST OF REFERENCE NUMERALS 1 component
2 component
3 medium
4 feeding device
5 microscope
6 control device
7 mixing chamber
8 mixing device
9 perfusion chamber
10 suction device
11 control device

What is claimed is:

1. A device for providing a predeterminable concentration of at least one component in a microscopic sample liquid medium, said device comprising:
   a microscope for imaging an image of a medium containing the at least one component and for processing the image to acquire measurement data of at least one measurement parameter of the medium containing the at least one component;
   a feeding device for feeding the at least one component, the feeding device including at least one of a titration and a pipettinq device; and
   a control device controlling the feeding device in a closed-loop control based on the measurement data to control that the medium contains the predeterminable concentration of the at least one component.

2. The device of claim 1, wherein the measurement parameter is the brightness in at least one of the medium, a predeterminable structure and a predeterminable region in the medium.

3. The device of claim 1, wherein the measurement parameter indicates when a change or a plurality of successive changes in the concentration of the at least one component should be started or stopped.

4. The device of claim 1, wherein the measurement parameter is the resolution with respect to at least one of a predeterminable structure and a predeterminable region in the medium.

5. The device of claim 1, wherein a measured quantity is the density of signals, the concentration having a direct influence on the measured quantity.

6. The device of claim 5, wherein the signals are fluorescence signals.

7. The device of claim 1, wherein the measurement parameter is a specific event or rate event with respect to at least one of a predeterminable structure and a predeterminable region in the medium.

8. The device of claim 7, wherein the measurement parameter indicates when a change or a plurality of successive changes in the concentration of the at least one component should be started or stopped.

9. The device of claim 1, wherein the feeding device includes at least one of a perfusor and a perfusion chamber.

10. Use of a device for providing a predeterminable concentration of at least one component in a microscopic sample liquid medium in microscopy applications using FAPs/biosensors, said device comprising: a microscope for imaging an image of a medium containing the at least one component and for processing the image to acquire measurement data of at least one measurement parameter of the medium containing the at least one component; a feeding device for feeding the at least one component, the feeding device including at least one of a titration and a pipetting device; and a control device controlling the feeding device in a closed-loop control based on the measurement data to control that the medium contains the predeterminable concentration of the at least one component.

11. Use of a device for providing a predeterminable concentration of at least one component in a microscopic sample liquid medium in a single particle tracking or a fluorescence correlation spectroscopy microscopy application, said device comprising: a microscope for imaging an image of a medium containing the at least one component and for processing the image to acquire measurement data of at least one measurement parameter of the medium containing the at least one component; a feeding device for feeding the at least one component, the feeding device including at least one of a titration and a pipettinq device;
   and a control device controlling the feeding device in a closed-loop control based on the measurement data to control that the medium contains the predeterminable concentration of the at least one component.

12. A method for providing a predeterminable concentration of at least one component in a microscopic sample liquid medium by a device including a feeding device for the at least one component, said method comprising:
   imaging an image of a medium containing the at least one component by a microscope;
   processing the image to acquire measurement data of at least one measurement parameter of the medium containing the at least one component;
   feeding the at least one component by the feeding device that includes at least one of a titration and a pipetting; and
   controlling the feeding device in a closed-loop control based on the measurement data to control that the medium contains the predeterminable concentration of the at least one component.

* * * * *